(12) United States Patent
Pellman

(10) Patent No.: US 9,645,136 B2
(45) Date of Patent: May 9, 2017

(54) METHODS OF TREATING A MEIOTIC KINESIN-ASSOCIATED DISEASE

(71) Applicant: DANA-FARBER CANCER INSTITUTE, INC., Boston, MA (US)

(72) Inventor: David Pellman, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 14/591,678

(22) Filed: Jan. 7, 2015

(65) Prior Publication Data
US 2015/0111786 A1    Apr. 23, 2015

Related U.S. Application Data

(62) Division of application No. 14/103,520, filed on Dec. 11, 2013, which is a division of application No. 12/994,920, filed as application No. PCT/US2009/045406 on May 28, 2009, now Pat. No. 8,629,118.

(60) Provisional application No. 61/057,590, filed on May 30, 2008.

(51) Int. Cl.
| | |
|---|---|
| C12Q 1/68 | (2006.01) |
| G01N 33/50 | (2006.01) |
| A61K 31/7088 | (2006.01) |
| A61K 31/7105 | (2006.01) |
| G01N 33/574 | (2006.01) |
| C12N 5/00 | (2006.01) |

(52) U.S. Cl.
CPC ...... *G01N 33/5011* (2013.01); *A61K 31/7088* (2013.01); *A61K 31/7105* (2013.01); *G01N 33/5026* (2013.01); *G01N 33/57496* (2013.01); *G01N 2333/914* (2013.01); *G01N 2500/02* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,439,196 A | 3/1984 | Hiauchi |
| 4,447,224 A | 5/1984 | DeCant, Jr. et al. |
| 4,447,233 A | 5/1984 | Mavfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,790,824 A | 12/1988 | Morrow et al. |
| 4,941,880 A | 7/1990 | Burns |
| 5,064,413 A | 11/1991 | McKinnon et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low et al. |
| 6,361,993 B1 | 3/2002 | Beraud |
| 6,410,254 B1* | 6/2002 | Finer et al. ............ 435/21 |
| 6,743,599 B1* | 6/2004 | Finer et al. ............ 435/21 |
| 2002/0165240 A1 | 11/2002 | Kimball et al. |
| 2003/0044900 A1* | 3/2003 | Beraud et al. ........... 435/69.1 |
| 2003/0220275 A1 | 11/2003 | Dobie et al. |
| 2005/0100508 A1 | 5/2005 | Nichols et al. |
| 2006/0257962 A1* | 11/2006 | Baliga et al. ........... 435/21 |
| 2007/0026424 A1 | 2/2007 | Powell et al. |
| 2007/0254310 A1* | 11/2007 | Finer et al. ............ 435/7.4 |
| 2008/0051463 A1 | 2/2008 | Gerlach et al. |

FOREIGN PATENT DOCUMENTS

| | | |
|---|---|---|
| JP | 2011/525174 A | 9/2011 |
| WO | WO-03/030832 A2 | 4/2003 |
| WO | WO-2008/015265 A1 | 2/2008 |
| WO | WO-2008/132752 A2 | 11/2008 |

OTHER PUBLICATIONS

Sickles et al. Toxicology and Applied Pharmacology vol. 222:111-121, 2007.*
Berge, Stephen M. et al., "Pharmaceutical Salts," Journal of Pharmaceutical Sciences, vol. 66(1):1-19 (1977).
Bloemen, P.G.M. et al., "Adhesion molecules: a new target for immunoliposome—mediated drug delivery," FEBS Letters, vol. 357:140-144 (1995).
Bodily, Kale D. et al., "A Novel Member of the Ig Superfamily, turtle, is a CNS-Specific Protein Required for Coordinated Motor Control," The Journal of Neuroscience, vol. 21(9):3113-3125 (2001).
Boveri, Theodor, The Origin of Malignant Tumors, The Williams & Wilkins Company, Baltimore, Waverly Press, Inc. (1929).
Brinkley, Bill R. et al., "Managing the centrosome numbers game: from chaos to stability in cancer cell division," Trends in Cell Biology, vol. 11(1):18-21 (2001).
Briscoe, Page et al., "Delivery of superoxide dismutase to pulmonary epithelium via pH-sensitive liposomes," Am. J. Physiol., vol. 268(3 Pt. 1):L374-L380 (1995).
Bulgheresi, Silvia et al., "Inscuteable-dependent apical localization of the microtubule binding protein Cornetto suggests a role in asymmetric cell division," Journal of Cell Science, vol. 114:3655-3662 (2001).

(Continued)

*Primary Examiner* — Sean McGarry
(74) *Attorney, Agent, or Firm* — Brinks Gilson & Lione

(57) ABSTRACT

The invention provides methods of treating a meiotic kinase-associated disease, preferably the meiotic kinase HSET, by administering an inhibitor of the meiotic kinase. Preferably, the disease is associated with the presence of supernumerary centrosomes, such as cancer. Methods of inhibiting the growth of a tumor cell by contacting the cell with an inhibitor of a meiotic kinase, preferably HSET, are also provided. Screening methods for identifying inhibitors of the meiotic kinase HSET are also provided. Methods of selecting subjects for treatment with an inhibitor of a meiotic kinase, such as HSET, are also provided.

10 Claims, 7 Drawing Sheets

(56) References Cited

OTHER PUBLICATIONS

Bushman, Frederic, "RNA Interference: Applications' in Vertebrates," Molecular Therapy, vol. 7(1):9-10 (2003).
Canman, Julie C. et al., "Microtubules suppress actomyosin-based cortical flow in Xenopus oocytes," Journal of Cell Science, vol. 110:1907-1917 (1997).
Chang, Paul et al., "Tankyrase-1 polymerization of poly(ADP-ribose) is required for spindle structure and function," Nature Cell Biology, vol. 7(11):1133-1139 (2005).
Chen, Jie-Guang et al., "Differential Mitotic Responses to Microtubule-stabilizing and -destabilizing Drugs," Cancer Research, vol. 62:1935-1938 (2002).
Chen, Ting et al., "N-terminal alpha-methylation of RCC1 is necessary for stable chromatin association and normal mitosis," Nature Cell Biology, vol. 9(5):596-603 (2007).
Chhabra, Ekta Seth et al., "INF2 Is a WASP Homology 2 Motif-containing Formin That Severs Actin Filaments and Accelerates Both Polymerization and Depolymerization," The Journal of Biological Chemistry, vol. 281(36):26754-26767 (2006).
Cottrell, Tricia R. et al., "Silence of the strands: RNA interference in eukaryotic pathogens," Trends in Microbiology, vol. 11(1):37-43 (2003).
D'Assoro, Antonino B. et al., "Amplified centrosomes in breast cancer: a potential indicator of tumor aggressiveness," Breast Cancer Research and Treatment, vol. 75:25-34 (2002).
Debonis, Salvatore et al., "In vitro screening for inhibitors of the human mitotic kinesin Eg5 with antimitotic and antitumor activities," Mol. Cancer Ther., vol. 3(9): 1079-1090 (2004).
Deluca, Jennifer G. et al., "Purification and Characterization of Native Conventional Kinesin, HSET, and CENP-E from Mitotic HeLa Cells," The Journal of Biological Chemistry, vol. 276(30):28014-28021 (2001).
Dixelius, Johan et al., "Endostatin Regulates Endothelial Cell Adhesin and Cytoskeletal Organization," Cancer Research, vol. 62:1944-1947 (2002).
Doxsey, Stephen. "Re-Evaluating Centrosome Function," Nature, vol. 2:688-698 (2001).
Deunsing, Stefan et al., "Human papillomaviruses and centrosome duplication errors: modeling the origins of genomic instability," oncogene, vol. 21:6241-6248 (2002).
Echard, Arnaud et al., "Terminal Cytokinesis Events Uncovered after an RNAi Screen," Curr. Biol., vol. 14(18):1685-1693 (2004).
Eggert, Ulrike S. et al., "Parallel Chemical Genetic and Genome-Wide RNAi Screens Identify Cytokinesis Inhibitors and Targets," PLoS Biology, vol. 2(12):2135-2143 e379 (2004).
Formstecher, Etienne et al., "Combination of Active and Inactive siRNA Targeting the Mitotic Kinesin Eg5 Impairs Silencing Efficiency in Several Cancer Cell Lines," Oligonucleotides, vol. 16:387-394 (2006).
Fukasawa, Kenji, "Oncogenes and tumour suppressors take on centrosomes," Nature Reviews Cancer, vol. 7:911-924 (2007).
Ganem, Neil J. et al., "Tetraploidy, aneuploidy and cancer," Current Opinion in Genetics & Development, vol. 17:157-162 (2007).
Giehl, M. et al., "Centrosome aberrations in chronic myeloid leukemia correlate with stage of disease and chromosomal instability," Leukemia, vol. 19:1192-1197 (2005).
Godinho, Susana A. et al., "Centrosomes and cancer: how cancer cells divide with too many centrosomes," Cancer Metastasis Rev., vol. 28:85-98 (2009).
Goshima, Gohta et al., "Genes Required for Mitotic Spindle Assembly in Drosophila S2 Cells," Science, vol. 316(5823):417-421 (2007).
Goshima, Gohta et al., "Mechanisms for focusing mitotic spindle poles by minus end-directed motor proteins," The Journal of Cell Biology, vol. 171(2):229-240 (2005).
Groen, Aaron C. et al., "A novel small-molecule inhibitor reveals a possible role of kinesin-5 in anastral a spindle-pole assembly," Journal of Cell Science, vol. 121:2293-2300 (2008).
Gupton, Stephanie L. et al., "Spatiotemporal Feedback between Actomyosin and Focal-Adhesion Systems Optimizes Rapid Cell Migration," Cell, vol. 125:1361-1374 (2006).
Heneen, Waheeb K., "In situ Analysis of Normal and Abnormal Patterns of the Mitotic Apparatus in Cultured Rat-Kangaroo Cells," Chromosoma, vol. 29:88-117 (1970).
Hirokawa, Nobutaka et al., "Kinesin Superfamily Proteins," Molecular Motors, Manfred Schliwa (ed.), Wiley-VCH Verlag GmbH & Co. KGaA, Weinheim, Chapter 3, pp. 79-109 (2003).
Karabay, A. et al., "Identification of Microtubule Binding Sites in the Ncd Tail Domain," Biochemistry, vol. 38:1838-1849 (1999).
Karsenti, E. et al., "The Mitotic Spindle: A Self-Made Machine," Science, vol. 294:543-547 (2001).
Keinanen, Kari et al., "Biosynthetic lipid-tagging of antibodies," FEBS Letters, vol. 346:123-126 (1994).
Killion, Jerald J. et al., "Systemic Targeting of Liposome-Encapsulated Immunomodulators to Macrophages for Treatment of Cancer Metastasis," Immunomethods, vol. 4:273-279 (1994).
Kwon, Mijung et al., "Mechanisms to suppress multipolar divisions in cancer cells with extra centrosomes," Genes & Development, vol. 22:2189-2203 (2008).
Levine, Douglas S. et al., "Formation of the tetraploid intermediate is associated with the development of cells with more than four centrioles in the elastase-simian virus 40 tumor antigen transgenic mouse model of pancreatic cancer," Proc. Natl. Acad. Sci. USA, vol. 88:6427-6431 (1991).
Lingle, Wilma L. et al., "Centrosome hypertrophy in human breast tumors: Implications for genomic stability and cell polarity," Proc. Natl. Acad. Sci. USA, vol. 95:2950-2955 (1998).
Mayer, Thomas U. et al., "Small Molecule Inhibitor of Mitotic Spindle Bipolarity Identified in a Phenotype-Based Screen," Science, vol. 286:971-974 (1999).
Mayr, Monika I. et al., "The Human Kinesin Kif18A is a Motile Microtubule Depolymerase Essential for Chromosome Congression," Current Biology, vol. 17:488-498 (2007).
McManus, Michael T. et al., "Gene Silencing in Mammals by Small Interfering RNAs," Nature Reviews Genetics, vol. 3:737-747 (2002).
Miki, "Analysis of the Kinesin Superfamily: Insights Into Structure and Function," *Trends in Cell Biology*, 15(9):467-476 (2005).
Miki, Harukata et al., "All kinesin superfamily protein, KIF, genes in mouse and human," PNAS, vol. 98(13):7004-7011 (2001).
Mitchison, T.J., "Actin based motility on retraction fibers in mitotic ptK2 cells," Cell Motil. Cytoskeleton, vol. 22(2): 135-151 (1992).
Morales-Mulia, Sandra et al., "Spindle Pole Organization in Drosophila S2 Cells by Dynein, Abnormal Spindle Protein (Asp), and KLP10A," Molecular Biology of the Cell, vol. 16:3176-3186 (2005).
Mosmann, Tim et al., "Rapid Colorimetric Assay for Cellular Growth and Survival: Application to Proliferation and Cytotoxicity Assays," Journal of Immunological Methods, vol. 65:55-63 (1983).
Mountain, Vicki et al., "The Kinesin-related Protein, HSET, Opposes the Activity of Eg5 and Cross-links Microtubules in the Mammalian Mitotic Spindle," The Journal of Cell Biology, vol. 147(2):351-365 (1999).
Munro, Edwin M., "PAR proteins and the cytoskeleton: a marriage of equals," Current Opinion in Cell Biology, vol. 18:86-94 (2006).
Nigg, ERich A., "Centrosome Aberrations: Cause or Consequence of Cancer Progression?" Nature Reviews Cancer, vol. 2:1-11 (2002).
Owais, Mohammad et al., "Chloroquine Encapsulated in Malaria-Infected Erythrocyte-Specific Antibody-Bearing Liposomes Effectively Controls Chloroquine-Resistant Plasmodium berghei Infections in Mice," Antimicrobial Agents and Chemotherapy, vol. 39(1):180-184 (1995).
Pihan, German A. et al., "Centrosome Abnormalities and Chromosome Instability Occur Together in Pre-invasive Carcinomas," Cancer Research, vol. 63:1398-1404 (2003).
Quintyne, Nicholas J, et al., "Spindle Multipolarity is Prevented by Centrosomal Clustering," Science, vol. 307:127-129 (2005).
Ranade, Vasant V, et al., "Drug Delivery Systems. 1, Site-Specific Drug Delivery Using Liposomes as Carriers," J. Clin. Pharmacol., vol. 29:685-694 (1989).

(56) References Cited

OTHER PUBLICATIONS

Rebacz, Blanka et al., "Identification of Griseofulvin as an Inhibitor of Centrosomal Clustering in a Phenotype-Based Screen," Cancer Res., vol. 67(13):6342-6350 (2007).
Ring, David et al., "Mitosis in a Cell with Multiple Centrioles," The Journal of Cell Biology; vol. 94:549-556 (1982).
Robinson, Joseph R. Sustained and Controlled Release Drug Delivery Systems, Marcel Dekker, Inc, New York (1978).
Rogalski, Teresa M. et al., "The UNC-112 Gene in Caenorhabditis elegans Encodes a Novel Component of Cell-Matrix Adhesion Structures Required for Integrin Localization in the Muscle Cell Membrane," The Journal of Cell Biology, vol. 150(1):253-264 (2000).
Schmidt, Mathias et al., "Mitotic drug targets and the development of novel anti-mitotic anticancer drugs," Drug Resistance Updates, vol. 10:162-181 (2007).
Schreiber, Valerie et al., "Poly(ADP-ribose): novel functions for an old molecule," Nature Reviews Molecular Cell Biology, vol. 7:517-528 (2006).
Schreier, Hans et al., "Targeting of Liposomes to Cells Expressing CD4 Using Glycosylphosphatidylinositol-anchored gp120," The Journal of Biological Chemistry, vol. 269(12):90901-9098 (1994).
Serman, A. et al., "GW body disassembly triggered by siRNAs independently of their silencing activity," Nucleic Acids Research, vol. 35(14):4715-4727 (2007).
Sharp, Phillip A. et al., "RNA Interference," Science, vol. 287:2431-2432 (2000).
Sluder, Greenfield et al., "The checkpoint control for anaphase onset does not monitor excess numbers of spindle poles or bipolar spindle symmetry," Journal of Cell Science, vol. 110:421-429 (1997).
Sluder, Greenfield et al., "The good, the bad and the ugly: the practical consequences to centrosome amplification," Current Opinion in Cell Biology, vol. 16:49-54 (2004).
Sousa, Aurea D. et al., "Myosin-X: a molecular motor at the cell's fingertip," Trends in Cell Biology, vol. 15(10):533-539 (2005).
Tepass, Ulrich et al., "Epithelial Cell Polarity and Cell Junctions in *Drosophila*," Annu. Rev. Genet., vol. 35:747-784 (2001).
Thery, Manuel et al., "Cell shape and cell division," Current Opinion in Cell Biology, vol. 18:648-657 (2006).
Thery, Manuel et al., "Experimental and theoretical study of mitotic spindle orientation," Nature, vol. 447:493-497 (2007).
Thery, Manuel et al., "The extracellular matrix guides the orientation of the cell division axis," Nature Cell Biology, vol. 7(10):947-953 (2005).
Toyoshima, Fumiko et al., "Integrin-mediated adhesion orients the spindle parallel to the substratum in an EB1- and myosin X-dependent manner," The EMBO Journal, vol. 26:1487-1498 (2007).
Tu, Yizeng et al., "Migfilin and Mig-2 Link Focal Adhesions to Filamin and the Actin Cytoskeleton and Function in Cell Shape Modulation," Cell, vol. 113:37-47 (2003).
Tuschl, Thomas et al., "Targeted mRNA degradation by double-stranded RNA in vitro," Genes & Development, vol. 13:3191-3197 (1999).
Umezawa, F. et al., "Liposome Targeting to Mouse Brain: Mannose as a Recognition Marker," Biochemical and Biophysical Research Communications, vol. 153(3)1038-1044 (1988).
Wakefield, James G. et al., "The *Drosophila* Protein Asp is Involved in Microtubule Organization during Spindle Formation and Cytokinesis," The Journal of Cell Biology, vol. 153(4):637-647 (2001).
Wakita, Kenichi et al., "Method for Screening Ecdysone-Inducible Stable Cell Lines," Bio Techniques, vol. 31(2):414-418 (2001).
Weber, Kari L. et al., "A microtubule-binding myosin required for nuclear anchoring and spindle assembly," Nature, vol. 431 :325-329-(2004).
Wei, Shu-Yi et al., "Echinoid is a Component of Adherens Junctions That Cooperates with DE-Cadherin to Mediate Cell Adhesion," Developmental Cell, vol. 8:493-504 (2005).
Wickstrom, Sara A. et al., "An Endostatin-derived Peptide Interacts with Integrins and Regulates Actin Cytoskeleton and Migration of Endothelial Cells," The Journal of Biological Chemistry, vol. 279(19):20178-20185 (2004).
Wilson, Anne P., "Cytotoxicity and viability assays," Animal Cell Culture, A Practical Approach, Third Edition, John R.W. Masters (Ed.), Oxford University Press, Oxford, Chpt. 7, pp. 175-219 (2000).
Zamore, Phillip D. et al., "RNAi: Double-Stranded RNA Directs the ATP-Dependent Cleavage of mRNA at 21 to 23 Nucleotide Intervals," Cell, vol. 101:25-33 (2000).
International Search Report for Application No. PCT/US2009/045406, dated Oct. 14, 2009.
International Preliminary Report on Patentability for Application No. PCT/US2009/045406, dated Nov. 30, 2010.
Examination Report dated May 31, 2013 in European Application No. 09767337.01-1464.
Office Action and English translation received in related Japanese Patent Application No. 2011-511802 dated Jan. 8, 2014.
Notice of Reasons for Rejection received in Japanese Patent Application No. 2015-020184 dated Mar. 3, 2016 and English translation thereof.

* cited by examiner

SEQUENCE LISTING

<160> NUMBER OF SEQ ID NOS: 15

<210> SEQ ID NO 1

```
<211> LENGTH: 21
<212> TYPE: RNA
<213> ORGANISM: Artificial Sequence
<220> FEATURE:
<223> OTHER INFORMATION: Synthetic siRNA oligonucleotide

<400> SEQUENCE: 1
uaacugaccc uuuaaguccu u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 2
aguguugugc gcucuguccu u                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 3
gacacaagca cgcaaguucu u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 4
ugguccaacg uuugaguccu u                                              21

<210> SEQ ID NO 5
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 5
caaguugaga uuuauguccu u                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 6
uaagacauca gcuacgacgu u                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 7
```
uaaucuacaa uucucccgcu u                                             21

<210> SEQ ID NO 8
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 8
auucccugaa auuccuccu u                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic siRNA Oligonucleotide
<220> FEATURE:
<221> NAME/KEY: misc_RNA
<222> LOCATION: (1)..(18)
<223> OTHER INFORMATION: RNA

<400> SEQUENCE: 9
ggcuaauaag aagugaagtt                                               20

<210> SEQ ID NO 10
<211> LENGTH: 21
<212> TYPE: DNA
<213> ORGANISM: Artificial Sequence
<220> FEATURE:
<223> OTHER INFORMATION: Synthetic siRNA Oligonucleotide
<220> FEATURE:
<221> NAME/KEY: misc_RNA
<222> LOCATION: (1)..(19)
<223> OTHER INFORMATION: RNA

<400> SEQUENCE: 10
ggaacugaag ggcaauauct t                                             21

<210> SEQ ID NO 11
<211> LENGTH: 21
<212> TYPE: DNA
<213> ORGANISM: Artificial Sequence
<220> FEATURE:
<223> OTHER INFORMATION: Synthetic siRNA Oligonucleotide
<220> FEATURE:
<221> NAME/KEY: misc_RNA
<222> LOCATION: (1)..(19)
<223> OTHER INFORMATION: RNA

<400> SEQUENCE: 11
ggccauuaac agcagucugt t                                             21

<210> SEQ ID NO 12
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 12
uuccacggug cccuugagcu u                                             21

<210> SEQ ID NO 13
<211> LENGTH: 21
<212> TYPE: RNA

```
<213> ORGANISM: Artificial Sequence
<220> FEATURE:
<223> OTHER INFORMATION: Synthetic siRNA Oligonucleotide

<400> SEQUENCE: 13
uucuccucgc uaucguuuuu u                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 14 uuucuuguqc agccagccuu u                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetic siRNA Oligonucleotide

<400> SEQUENCE: 15
uacaucagcu ucgacuggcu u                                              21
```

METHODS OF TREATING A MEIOTIC KINESIN-ASSOCIATED DISEASE

RELATED APPLICATIONS

The present patent document claims priority to application Ser. No. 14/103,520, filed Dec. 11, 2013, which is a divisional application of application Ser. No. 12/994,920, filed Apr. 7, 2011, which is a §371 national phase application of PCT Application Serial No. PCT/US2009/045406, filed May 28, 2009, designating the United States and published in English, which claims the benefit of the filing date under 35 U.S.C. §119(e) of Provisional U.S. Patent Application Ser. No. 61/057,590, filed May 30, 2008. All of the foregoing applications are hereby incorporated by reference.

BACKGROUND OF THE INVENTION

Centrosomes play a crucial role in the equal segregation of chromosomes by contributing to bipolar spindle assembly during mitosis (Doxsey, S. (2001) *Nat Rev Mol Cell Biol* 2:688-698). The tight control on centrosome duplication, limiting it to once per cell cycle, ensures that normal cells enter mitosis with two centrosomes or microtubule organizing centers (MTOCs). Failure to properly control centrosome number and function can lead to multipolar spindles, aneuploidy, disruption of cell polarity, and failure of asymmetric cell divisions (Heneen, W. K. (1970) *Chromosoma* 29:88-117; Nigg, E. A. (2002) *Nat Rev Cancer* 2:815-825).

Increased centrosome number, often termed centrosome amplification, is a common characteristic of solid and hematological cancers. Centrosome amplification correlates with aneuploidy and malignant behavior in tumor cell lines, mouse tumor models, and human tumors (D'Assoro, A. B. et al. (2002)*Breast Cancer Res Treat* 75: 25-34; Giehl, S. et al. (2005) *Leukemia* 19:1192-1197; Levine, D. S. et al. (1991) *Proc Natl Acad Sci USA* 88:6427-6431; Lingle, W. L. et al. (1998) *Proc Natl Acad Sci USA* 95:2950-2955; Pihan, G. A. et al. (2003) *Cancer Res* 63:1398-1404). Mutation or misregulation of a variety of tumor suppressors or oncogenes are correlated with centrosome amplification (Fukasawa, K. (2007) *Nat Rev Cancer* 7:911-924). Centrosome amplification can, in principle, arise from several types of cell division errors: centrosome overduplication, de novo synthesis of centrosomes, cell fusion, or cytokinesis failure (Boveri, T. (1929) *The Origin of Malignant Tumors* (Baltimore: Williams and Wilkins); Ganem, N. J. et al. (2007) *Curr Opin Genet Dev* 17:157-162; Nigg, E. A. (2002) *Nat Rev Cancer* 2:815-825).

The role of supernumerary centrosomes in tumor biology is likely to be multifaceted. Whereas multiple centrosomes might facilitate tumorigenesis by promoting aneuploidy and/or disrupting cell polarity, they may also impose a fitness cost on the growth of mature cancers because of the potential for multipolar mitoses. To circumvent this problem, many cancer cells appear to have mechanisms that suppress multipolar mitoses, the best studied being clustering of supernumerary centrosomes into two groups enabling a bipolar mitosis (Brinkley, B. R. (2001) *Trends Cell Biol* 11:18-21; Nigg, E. A. (2002) *Nat Rev Cancer* 2:815-825; Ring, D. et al. (1982) *J Cell Biol* 94:549-556).

Centrosome clustering in tumor cells is incompletely understood, however, it is expected to rely to a significant degree on microtubule-associated proteins (MAPs) and motors that organize the spindle poles (Karsenti, E. and Vernos, I. (2001) *Science* 294:543-547; Nigg, E. A. (2002) *Nat Rev Cancer* 2:815-825). For example, recent work uncovered a requirement of cytoplasmic dynein, a minus end-directed microtubule (MT) motor, and NuMA, a spindle associated MAP, in centrosome clustering (Quintyne, N. J. et al. (2005) *Science* 307:127-129). The existence of mechanisms that suppress multipolar mitoses raises the possibility of a novel therapeutic strategy for cancer: drugs that interfere with centrosome clustering mechanisms could be lethal to tumor cells containing multiple centrosomes, but potentially spare normal cells. Although several drugs, including Taxol, can promote multipolar mitosis, none are specific for cells with multiple centrosomes (Chen, J. G. and Horwitz, S. B. (2002) *Cancer Res* 62:1935-1938; Rebacz, B. et al. (2007) *Cancer Res* 67:6342-6350).

Accordingly, identification of components involved in the centrosome clustering mechanisms in tumor cells is still needed.

SUMMARY OF THE INVENTION

The present invention identifies a key component involved in the centrosome clustering mechanism in tumor cells and demonstrates that centrosome declustering, by inhibition of this component, can induce cell death selectively in cells with supernumerary centrosomes. This key component, the meiotic kinesin HSET (a kinesin-14 family member), is not essential for mitosis in normal cells but is demonstrated herein to be essential for the survival of cancer cells with extra centrosomes. Accordingly, the present invention provides a target for selective killing of cells containing extra centrosomes, such as cancer cells, while avoiding killing of normal cells.

Thus, in one aspect, the invention pertains to a method of treating a meiotic kinesin-associated disease or disorder, comprising administering to a subject in need of treatment thereof an agent which inhibits a meiotic kinesin such that treatment of the disease or disorder is achieved. In one embodiment, the disease or disorder is an autosomal disease or disorder. In a preferred embodiment, the disease or disorder is a centrosomal disease or disorder (e.g., characterized by the presence of supernumerary centrosomes). In another preferred embodiment, the disease or disorder is a cellular proliferative disease, such as cancer or malignancy. Preferably, the meiotic kinesin is a member of the kinesin-14 family, most preferably HSET. Examples of suitable agents for inhibiting the meiotic kinesin include RNAi agents and small molecules. In one embodiment, the agent inhibits the ATPase activity of the kinesin. In another embodiment, the agent inhibits the microtubule binding activity of the kinesin. The agent can be administered, for example, orally or parentally.

In another aspect, the invention pertains to a method of inhibiting growth of a tumor cell in which cellular proliferation is associated with a meiotic kinesin, comprising contacting the tumor cell with an agent which inhibits a meiotic kinesin such that growth of the tumor cell is inhibited. In a preferred embodiment, the tumor cell comprises supernumerary centrosomes. Preferably, the meiotic kinesin is a member of the kinesin-14 family, most preferably HSET. Examples of suitable agents for inhibiting the meiotic kinesin include RNAi agents and small molecules. In one embodiment, the agent inhibits the ATPase activity of the kinesin. In another embodiment, the agent inhibits the microtubule binding activity of the kinesin. The tumor cell can be contacted with the agent by, for example, culturing the tumor cell with the agent or by directly injecting the agent into a tumor that contains the tumor cell or by administering the agent to a subject bearing a tumor that contains the tumor cell.

In another aspect, the invention pertains to a method of inhibiting proliferation of a cell in which cellular proliferation is associated with a meiotic kinesin, comprising contacting the cell with an agent which inhibits a meiotic kinesin such that inhibition of cell proliferation is achieved. In a preferred embodiment, the cell contains supernumerary centrosomes. Preferably, the meiotic kinesin is a member of the kinesin-14 family, most preferably HSET. Examples of suitable agents for inhibiting the meiotic kinesin include RNAi agents and small molecules. In one embodiment, the agent inhibits the ATPase activity of the kinesin. In another embodiment, the agent inhibits the microtubule binding activity of the kinesin.

In yet another aspect, the invention pertains to a method for identifying a compound that inhibits activity of a meiotic kinesin HSET, the method comprising providing an indicator composition comprising the meiotic kinesin HSET;

contacting the indicator composition with a test compound; and determining activity of the meiotic kinesin HSET in the presence of the test compound, wherein reduction of activity of the meiotic kinesin HSET in the presence of the test compound, as compared to activity of the meiotic kinesin HSET in the absence of the test compound, identifies the test compound as a compound that inhibits the activity of a meiotic kinesin HSET.

In a preferred embodiment, the indicator composition is contacted with each member of a library of test compounds and one or more test compounds within the library are selected that inhibit the activity of the meiotic kinesin HSET.

In one embodiment, the activity of the meiotic kinesin HSET is determined by measuring the ATPase activity of the kinesin. In another embodiment, the activity of the meiotic kinesin HSET is determined by measuring the microtubule binding activity of the kinesin. In yet another embodiment, the activity of the meiotic kinesin HSET is determined by measuring the expression of HSET mRNA or protein.

The invention also pertains to isolated compounds identified by the screening methods of the invention.

In yet another aspect, the invention pertains to a method of selecting a subject with a tumor for treatment with an agent which inhibits a meiotic kinesin, the method comprising (i) obtaining a tumor cell sample from the subject, and (ii) determining centrosome number in the tumor cell sample, wherein presence of supernumerary centrosomes in the tumor cell sample selects the subject for treatment with an agent which inhibits a meiotic kinesin. Preferably, the meiotic kinesin is a member of the kinesin-14 family, most preferably HSET. Preferably, at least 50% of the tumor cells in the sample contain supernumerary centrosomes, more preferably at least 75% of the tumor cells in the sample contain supernumerary centrosomes and even more preferably at least 90% of the tumor cells in the sample contain supernumerary centrosomes.

DETAILED DESCRIPTION

Figure 1:
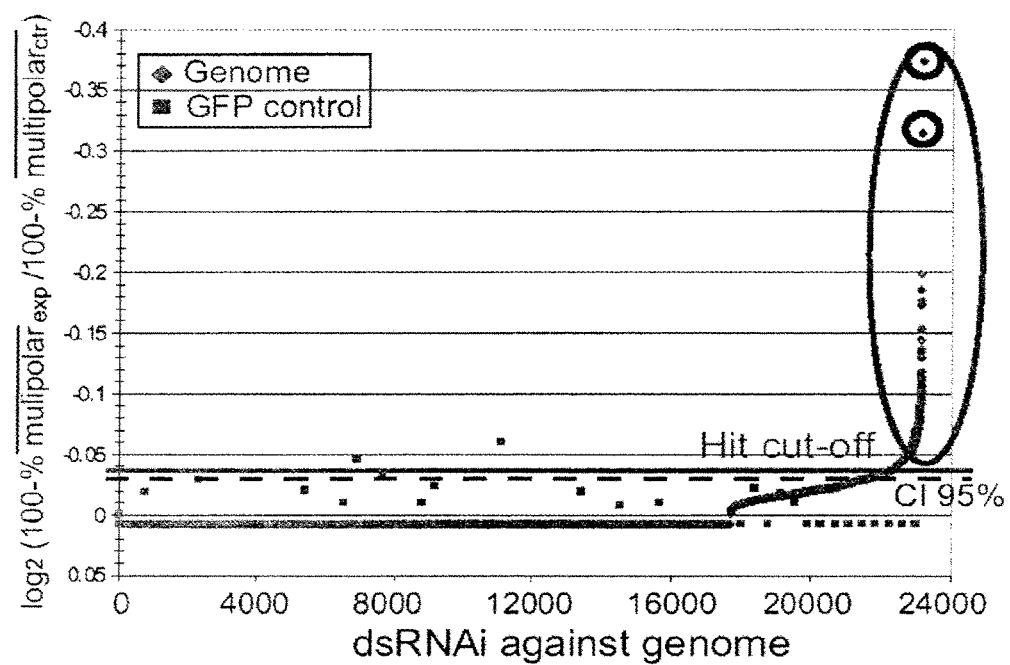
FIG. 1 shows the scheme for the genome-wide RNAi screen in *Drosophila* S2 cells to identify genes whose knockdown leads to multipolar spindles (centrosome de-clustering).

The present invention identifies a key component involved in the centrosome clustering mechanism in tumor cells. The present invention further demonstrates that centrosome declustering can induce cell death selectively in cells with supernumerary centrosomes. In at least one embodiment, the present invention is based, at least in part, on the discovery that the meiotic kinesin HSET, a normally nonessential kinesin motor, is required for the viability of cells containing extra centrosomes. Multiple centrosomes in tumor cells create the potential for multipolar divisions that can lead to aneuploidy and cell death. Nevertheless, many cancer cells successfully divide because of mechanisms that suppress multipolar mitoses. A genome-wide RNAi screen in *Drosophila* S2 cells and a secondary analysis in cancer cells defined mechanisms that suppress multipolar mitoses. In particular, the meiotic kinesin HSET now has been shown to be essential for the viability of certain extra centrosome-containing cancer cells, with inhibition of HSET leading to inhibition of cell viability (see in particular Examples 6 and 8 herein). Thus, the finding described herein that the minus end-directed motor HSET is essential for clustering extra centrosomes provides a new therapeutic strategy: blocking centrosome clustering and promoting multipolar mitoses to selectively induce death in tumors with a high proportion of cells containing multiple centrosomes. The present invention provides for assays to identify agents that modulate the activity of a meiotic kinesin, such as HSET, as well as methods of treating diseases or disorders associated with meiotic kinesin activity, and methods of selecting subjects for treatment with a meiotic kinesin inhibitor.

So that the invention may be more readily understood, certain terms are first defined.

The term "kinesin" refers to a class of motor proteins found in eukaryotic cells that are capable of moving along microtubules powered by the hydrolysis of ATP. The term "meiotic kinesin" refers to kinesins that are involved in, and necessary for, the cellular function of meiosis.

The term "kinesin-14 family member" refers to a kinesin that is a member of the kinesin-14 family, which family shares a common C-terminal motor domain differing from other kinesin proteins. The kinesin-14 family is also known in the art as the C-terminal kinesins. Non-limiting examples of kinesin-14 family members include *Homo sapiens* proteins HSET, CHO2, KIFC2 and KIFC3, *Mus musculus* proteins HSET and KIFC2, *Drosophila melanogaster* protein Ned and *Saccharomyces cerevisiae* protein Kar3.

The term "HSET" refers to a kinesin-14 family member also known in the art as KIFC1 (kinesin family member C1). The mRNA and protein sequence of human HSET are available at Genbank Accession Nos. NM_002263 and NP_002254, respectively. The mRNA and protein sequence of mouse HSET are available at Genbank Accession Nos. NM_053173 and NP_444403, respectively. A human HSET sequence may differ from human HSET of Genbank Accession Number NP_002254 by having, for example, conserved mutations or mutations in non-conserved regions and the HSET has substantially the same biological function as the human HSET of Genbank Accession Number NP_002254. A particular human HSET sequence will generally be at least 90% identical in amino acids sequence to human HSET, such as to Genbank Accession Number NP_002254, and contains amino acid residues that identify the amino acid sequence as being human when compared to HSET amino acid sequences of other species (e.g., murine). In certain cases, a human HSET may be at least 95%, or even at least 96%, 97%, 98%, or 99% identical in amino acid sequence to human HSET, such as to Genbank Accession Number NP_002254. In certain embodiments, a human HSET sequence will display no more than 10 amino acid differences from the human HSET sequence, such as to Genbank Accession Number NP_002254. In certain embodiments, the human HSET may display no more than 5, or even no more than 4, 3, 2, or 1 amino acid difference from the human HSET sequence, such as to Genbank Accession Number NP_002254.

The term "meiotic kinesin-associated disease or disorder" is intended to refer to a disease or disorder the pathogenesis of which requires the activity of a kinesin known to function in meiosis.

The term "autosomal disease or disorder" is intended to refer to a disease or disorder the pathogenesis of which is associated with a non-sex chromosome.

The term "centrosomal disease or disorder" is intended to refer to a disease or disorder the pathogenesis of which is associated with alteration in the number or activity of centrosomes.

The term "supernumerary centrosomes" is intended to refer to more than the usual or prescribed number of centrosomes in a cell, typically more than the usual number of two centrosomes in a cell.

The term "cellular proliferative disease or disorder" is intended to refer to a disease or disorder the pathogenesis of which is associated with altered or aberrant cellular proliferation.

As used herein, an agent or compound that "inhibits activity" of a meiotic kinesin, such as HSET, is intended to refer to an agent or compound that reduces, or decreases, or lessens the activity of the meiotic kinesin, which inhibition can be partial or complete, and wherein such "activity" can be, for example, expression of the mRNA encoding the kinesin in a cell, expression of the protein level of the kinesin in a cell, or expression of the enzymatic activity or other biological activities of the kinesin, examples of such enzymatic and other biological activities including, but not being limited to, ATPase activity and microtubule binding activity.

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

As used herein, an "antisense" nucleic acid comprises a nucleotide sequence that is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, an "RNAi agent" refers to an agent, such as a nucleic acid molecule, that mediates RNA interference. RNA interference (RNAi) is a post-transcriptional, targeted gene-silencing technique that uses double-stranded RNA (dsRNA) to degrade messenger RNA (mRNA) containing the same sequence as the dsRNA (see e.g., Sharp, P. A. and Zamore, P. D. (2000) *Science* 287:2431-2432; Zamore, P. D., et al. (2000) *Cell* 101:25-33; Tuschl, T. et al. (1999) *Genes Dev.* 13:3191-3197; Cottrell T. R., and Doering T. L. (2003) *Trends Alicrobiol.* 11:37-43; Bushman F. (2003) *Mol Therapy* 7:9-10; McManus M. T. and Sharp P. A. (2002) *Nat Rev Genet.* 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of siRNA are commercially available, e.g. from New England Biolabs, Dharmacon or Ambion. Thus, in one embodiment, an "RNAi agent" is a nucleic acid molecule that is an siRNA molecule. Other examples of nucleic acid molecules that can be used to silence gene expression via RNA interference include small hairpin RNA (shRNA) and microRNA (miRNA). Accordingly, the term "RNAi agent" also is intended to encompass molecules such as shRNA, miRNA and the like that can be used to silence gene expression by RNA interference.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Methods of Treating Diseases or Disorders

In one aspect, the invention pertains to methods for treating diseases or disorders. In particular, the invention provides a method of treating a meiotic kinesin-associated disease or disorder. The method comprises administering to a subject in need of treatment thereof an agent which inhibits a meiotic kinesin such that treatment of the disease or disorder is achieved.

Preferably, the disease or disorder is an autosomal disease or disorder. More preferably, the disease or disorder is a centrosomal disease or disorder. Even more preferably, the disease or disorder is a cellular proliferative disease or disorder. Most preferably, the disease or disorder is a cancer, tumor or other malignancy. Preferably, the cancer, tumor or other malignancy is one in which the cancer, tumor or malignant cells comprise supernumerary centrosomes. More preferably, at least 50% of the cancer, tumor or malignant cells comprise supernumerary centrosomes, even more preferably at least 75% of the cancer, tumor or malignant cells comprise supernumerary centrosomes, and even more preferably at least 90% of the cancer, tumor or malignant cells comprise supernumerary centrosomes. Non-limiting examples of cancers which can be treated according to the methods of the invention include breast, colon, lung, prostate, ovarian, pancreatic, brain, stomach, renal, hepatic, bone, skin, leukemias, lymphomas, multiple myeloma and melanoma.

Other diseases or disorders associated with the accumulation of supernumerary centrosomes include human papillomavirus (HPV) infection, including HPV-associated cervical neoplasias (see e.g., Duensing, S. and Munger, K. (2002) *Oncogene* 21:6241-6248), Preferably, the meiotic kinesin is a kinesin-14 family member. More preferably, the meiotic kinesin is HSET.

Any agent that inhibits the activity of the meiotic kinesin, e.g., HSET, and that is suitable for use in the subject can be used in the treatment methods of the invention. In a preferred embodiment, the agent is an RNAi agent, such as an siRNA. As described in detail in Examples 6 and 8, siRNA inhibitors of human HSET were demonstrated to reduce viability of several different cancer cell lines. Nonlimiting examples of nucleic acid molecules that can function as siRNA inhibitors of human HSET include the oligonucleotides shown in SEQ ID NOs: 1-4. Other agents that can be used to inhibit the activity of a meiotic kinesin, e.g., HSET, include, but are not limited to, antisense molecules and small molecule inhibitors (e.g., small organic molecules). Such agents can be identified, for example, using screening assays for HSET inhibitors as described in detail herein. In one embodiment, the agent inhibits the ATPase activity of the kinesin. In another embodiment, the agent inhibits the microtubule binding activity of the kinesin.

An agent of the invention typically is administered to the subject in a pharmaceutical composition. Administration is by any route suitable to accomplish the desired treatment. For example, in one embodiment, the agent is administered orally. In another embodiment, the agent is administered parenterally.

The pharmaceutical composition typically includes the agent formulated together with a pharmaceutically acceptable carrier. Pharmaceutical compositions can be administered in combination therapy, i.e., combined with other agents. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for oral, intravenous, intramuscular, subcutaneous, parenteral, spinal or epidermal administration (e.g., by injection or infusion). Depending on the route of administration, the active agent may be coated in a material to protect the agent from the action of acids and other natural conditions that may inactivate the agent.

The pharmaceutical composition may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A pharmaceutical composition can be administered via one or more routes of administration using one or more of a variety of methods known in the art. As will be appreciated by the skilled artisan, the route and/or mode of administration will vary depending upon the desired results. Preferred routes of administration include oral, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, a therapeutic composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the pharmaceutical compositions can be formulated to ensure proper distribution in vivo. For example, the blood-brain barrier (BBB) excludes many highly hydrophilic compounds. To ensure that the therapeutic agent crosses the BBB (if desired), it can be formulated, for example, in liposomes. For methods of manufacturing Liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Inhibition of Cell Growth or Proliferation

In another aspect, the invention pertains to methods of inhibiting cell growth. For example, the invention provides a method of inhibiting growth of a tumor cell in which cellular proliferation is associated with a meiotic kinesin, comprising contacting the tumor cell with an agent which inhibits a meiotic kinesin such that growth of the tumor cell is inhibited. Preferably, the tumor cell comprises supernumerary centrosomes. Preferably, the meiotic kinesin is a kinesin-14 family member, most preferably HSET. The agent can be, for example, an RNAi agent, an antisense molecule or a small molecule, as described in further detail above. In one embodiment, the agent inhibits the ATPase activity of the kinesin. In another embodiment, the agent inhibits the microtubule binding activity of the kinesin.

The tumor cell can be contacted with the agent by, for example, culturing the tumor cell with the agent. Additionally or alternatively, the tumor cell can be contacted with the agent by directly injecting the agent into a tumor that contains the tumor cell. Additionally or alternatively, the tumor cell can be contacted with the agent by administering the agent to a subject bearing a tumor that contains the tumor cell.

In another aspect, the invention provides a method of inhibiting proliferation of a cell in which cellular proliferation is associated with a meiotic kinesin, comprising contacting the cell with an agent which inhibits a meiotic kinesin such that inhibition of cell proliferation is achieved. Preferably, the cell contains supernumerary centrosomes. Preferably, the meiotic kinesin is a kinesin-14 family member, most preferably HSET. The agent can be, for example, an RNAi agent, an antisense molecule or a small molecule, as described in further detail above. In one embodiment, the agent inhibits the ATPase activity of the kinesin. In another embodiment, the agent inhibits the microtubule binding activity of the kinesin.

The cell can be contacted with the agent by, for example, culturing the cell with the agent. Additionally or alternatively, the cell can be contacted with the agent by directly injecting the agent into a tumor that contains the cell. Additionally or alternatively, the cell can be contacted with the agent by administering the agent to a subject bearing the cell.

Screening Methods

In another aspect, the invention pertains to methods of identifying compounds that inhibit the activity of a meiotic kinesin, such as HSET. For example, the invention provides a method for identifying a compound that inhibits activity of a meiotic kinesin HSET, the method comprising providing an indicator composition comprising the meiotic kinesin HSET;

contacting the indicator composition with a test compound; and determining activity of the meiotic kinesin HSET in the presence of the test compound, wherein reduction of activity of the meiotic kinesin HSET in the presence of the test compound, as compared to activity of the meiotic kinesin HSET in the absence of the test compound, identifies the test compound as a compound that inhibits the activity of a meiotic kinesin HSET.

The indicator composition can be, for example, a cell that contains (i.e., expresses) HSET or a cell-free composition that contains HSET. If the indicator composition is a cell that contains (i.e., expresses) HSET, it can be a cell that naturally expresses HSET or a cell that has been engineered (e.g., by standard recombinant DNA techniques) to express or overexpress HSET. Cells that naturally express HSET include, but are not limited to, the cancer cell lines MDA-231, MMEDX 4N and N1E-115, as well as other cell lines described in the Examples. To engineer a cell line to express human HSET, the human HSET cDNA (having the sequence set forth in Genbank Accession No. NM_002263) can be obtained by standard methods (e.g., PCR amplification), inserted into an expression vector and transfected into a host cell, using standard recombinant DNA techniques. To obtain HSET in a cell-free composition, HSET can be purified using methods known in the art. For example, DeLuca, J. G. et al. (2001) J. Biol. Chem. 276:28014-28021 describe the purification of human HSET from HeLa cells. Anti-HSET antibodies have been described in the art which can be used to purify HSET by standard immunoaffinity techniques.

The "contacting" step of the method can comprise, for example, incubation of the test compound with a cell that contains (i.e., expresses) HSET or incubation of the test compound with a cell-free composition that contains HSET.

The step of "determining activity of the meiotic kinesin HSET" can be carried out using one or more of a variety of possible "read-outs." For example, in one embodiment, the activity of HSET is determined by measuring HSET mRNA levels in a cell that expresses HSET, wherein a test compound is an inhibitor of HSET activity if it reduces the level of expression of HSET mRNA as compared to the level in the absence of the test compounds. Methodologies for measuring HSET mRNA levels are well established in the art, including but not limited to Northern blot analysis and PCR amplification methods. In another embodiment, the activity of HSET is determined by measuring HSET protein levels in a cell that expresses HSET, wherein a test compound is an inhibitor of HSET activity if it reduces the level of expression of HSET protein as compared to the level in the absence of the test compounds. Methodologies for measuring HSET protein levels are well established in the art, including but not limited to Western blot analysis and immunoprecipitation methods.

In yet other embodiments, the activity of HSET is determined by measuring one or more enzymatic or biological activities of HSET. For example, purified HSET has been demonstrated to produce microtubule gliding when Taxol-stabilized microtubules are contacted with purified HSET (see DeLuca, J. G. et al. (2001) J. Biol. Chem. 276:28014-28021). Thus, in one embodiment, the effect of a test compound on HSET-mediated microtubule gliding in vitro can be determined, as compared to HSET-mediated microtubule gliding in the absence of the test compound, to thereby determine the effect of the test compound on HSET activity.

Additionally or alternatively, the effect of a test compound on HSET ATPase activity can be determined. For example, DeBonis, S. et al. (2004) Mol. Cancer Ther. 3:1079-1090 describe a microtubule-activated ATPase assay used to identify inhibitors of the mitotic kinesin Eg5. Similarly, such a microtubule-activated ATPase assay can be used with purified HSET to determine the effect of a test compound on the ATPase activity of HSET. Thus, in one embodiment, the activity of the meiotic kinesin HSET is determined by measuring the ATPase activity of the kinesin.

Other biological activities of HSET that can be used as "read-outs" in determining the effect of a test compound on HSET activity include, but are not limited to, microtubule binding activity and centrosome clustering activity. Thus, in other embodiments, the activity of the meiotic kinesin HSET is determined by measuring the microtubule binding activity or centrosome clustering activity of the kinesin.

It has been discovered that overexpression of the HSET gene in cells leads to growth arrest and cell death. Accordingly, the invention also provides cell-based assays to determine the effect of a test compound upon HSET-induced growth arrest and cell death, and thereby identify modulators (e.g., inhibitors) of HSET. Generally, these assays include the steps of: (a) providing an indicator cell comprising a recombinant expression vector comprising an HSET gene operably linked to a promoter, under conditions whereby said HSET gene is expressed in said indicator cell; (b) contacting said indicator cell with a test compound; and (c) determining the effect of the test compound on HSET-induced growth arrest and cell death, wherein attenuation of HSET-induced growth arrest and cell death in the presence of the test compound, as compared to HSET-induced growth arrest and cell death in the absence of the test compound, identifies the test compound as a compound that inhibits the activity of the meiotic kinesin, HSET. In one embodiment, the promoter is an inducible promoter. Any art recognized inducible promoter system is considered, including but not limited to, an ecdysone inducible system (see, for example, Wakita et al., 2001, Biotechniques 31:414). Methodologies for measuring cell proliferation and cell viability are well known in the art (see, for example, Wilson, A. P., *Cytotoxicity and Viability Assays* in Animal Cell Culture: A Practical Approach, 3rd ed. (ed. Masters, J. R. W.) Oxford University Press: oXford 2000, Vol. 1; and Mosmann, T., Rapid Colorimetric Assay for Cellular Growth and Survival: Application to Proliferation and Cytotoxicity Assays. J. Immunol. Meth. 1983, 65, 55-63.).

In a preferred embodiment, a library of compounds is screened in the screening assay of the invention to identify compounds within the library that exhibit the ability to inhibit the activity of HSET. Thus, in a preferred embodiment, the indicator composition described above is contacted with each member of a library of test compounds and one or more test compounds within the library are selected that inhibit the activity of the meiotic kinesin HSET.

In yet another aspect, the invention pertains to isolated compounds identified by the screening methods of the invention.

Methods of Selecting Subjects

In another aspect, the invention pertains to methods of selecting subjects for treatment with an agent that inhibits a meiotic kinesin, such as HSET. As demonstrated herein, inhibition of HSET activity selectively reduces the viability of cells, such as cancer cells, that contain extra centrosomes. Accordingly, subjects bearing a tumor containing cells with extra centrosomes are of particular interest for treatment with an agent that inhibits a meiotic kinesin, such as HSET. Thus, in another aspect, the invention provides a method of selecting a subject with a tumor for treatment with an agent which inhibits a meiotic kinesin, the method comprising (i) obtaining a tumor cell sample from the subject, and (ii) determining centrosome number in the tumor cell sample, wherein presence of supernumerary centrosomes in the tumor cell sample selects the subject for treatment with an agent which inhibits a meiotic kinesin. Methods for determining centrosome numbers in cells are well known in the art and can be applied to this subject selection method. For example, centrosomes can be fluorescently stained using an anti-gamma tubulin antibody and a fluorescently-labeled secondary antibody, followed by immunofluorescence imaging to quantitate the number of centrosomes per cell (described further in the Examples).

Preferably, the meiotic kinesin is a kinesin-14 family member, more preferably HSET. Preferably, at least 50% of tumor cells in the tumor cell sample contain supernumerary centrosomes. More preferably, at least 75% of tumor cells in the tumor cell sample contain supernumerary centrosomes. Even more preferably, at least 90% of tumor cells in the tumor cell sample contain supernumerary centrosomes.

The present invention is further illustrated by the following examples, which should not be construed as further limiting. The contents of all references, Genbank entries, patents and published patent applications cited throughout this application are expressly incorporated herein by reference in their entirety.

Example 1

Identification of Therapeutic Targets for the Treatment of Meiotic Kinesin Associated Diseases or Disorders In this example, an RNAi screen was used to comprehensively define the molecular pathways required for clustering supernumerary centrosomes. Of 8 *Drosophila* cell lines characterized, the near-tetraploid S2 cells were most suitable for the screen because >50% of cells contain extra centrosomes which are efficiently clustered into two poles during mitoses. The scheme for the genome-wide screening is illustrated in FIG. 1, which provides details of the procedures for the primary and secondary screens.

23,172 dsRNAs targeting ~99% of the *Drosophila* genome (~14,000 genes) were screened to identify genes whose knockdown leads to multipolar spindles (centrosome de-clustering) in S2 cells. S2 cells were exposed to dsRNA for 4 days and mitotic figures were enriched by treatment with the proteasome inhibitor MG132 during the last 9 hours of the RNAi treatment. Cells were stained for DNA, microtubules (MTs) and centrosomes, and images were acquired with a 20× objective, using a high throughput automated microscope.

More specifically, S2 cells were plated at a density of $1 \times 10^4$ cells/well in serum-free Schneider's medium in 384 well plates which were pre-plated with 0.25 µg dsRNA (dsRNAs are available at the *Drosophila* RNAi Screening Center, DRSC, http://flyrnai.org). Cells were incubated with dsRNA for 40 minutes at room temperature (RT) in serum free medium, followed by addition of serum-containing medium and incubated for 3.5 days to allow for protein depletion. To block the metaphase-anaphase transition, 25 µM MG132, a proteasome inhibitor, was added at the end of the RNAi treatment (3.5 day-RNAi treated cells) and incubated for an additional 9 hours (total of approximately 4 day RNAi incubation). To facilitate the attachment of mitotic cells, RNAi treated cells were resuspended, transferred to new 384 well plates that were pre-coated with Concanavalin A (Con-A, 0.25 mg/ml), and the plates were spun at 1.000 rpm for 1 minute. Cells were fixed in 4% paraformaldehyde (PFA) in PBS (pH 7.2), permeabilized with PBS-Triton 0.01% (PBST), incubated with 0.5% SDS in PBST, and kept in PBST at 4° C. until proceeding to immunostaining.

For the primary screen, the fixed cells were stained for MTs and centrosomes with FITC-anti-alpha tubulin (DM1A, 1:300, Sigma) and mouse anti-gamma tubulin (GTU88, 1:500) antibodies, respectively. Alexa Fluor 568 or 594 Donkey anti-mouse IgG was used as secondary antibodies (1:1000). Cells were stained for DNA with Hoechst 33342 (1:5000, Invitrogen) in PBST and stored in the same solution at 4° C.

For the primary screen, cells were imaged using an automated microscope, either the ImageXpress Micro (Molecular Devices, ICCB, inverted fully automated epifluorescent microscope, laser auto-focus, equipped with the Photometrics CoolSNAP ES digital CCD camera, MetaXpress for analysis), or the Discovery-1 (Molecular Devices, DRSC, automated filter and dichroic wheels and six objective turret, high-speed laser auto-focus, and can measure up to eight fluorophores per assay in multi-well plates), using a 20× air objective. Auto-focusing was performed on FITC (MTs) and images were acquired from single focal plane for three channels (Hoechst, Cy3, and FITC).

The secondary screen was performed in 96 well plates (1 μg dsRNA/well for $5×10^4$ cells/well) and followed almost the same methodology as the primary screen. At the end of RNAi, cells were transferred to 96 well glass-bottom plates (Whatman) for high resolution imaging. Cells were stained additionally to identify mitotic cells with anti-rabbit phospho-histone H3 and Alexa Fluor 660 Donkey anti-rabbit IgG. To ensure imaging of all centrosomes, 3D images were taken with a Zeiss Axiovert microscope and Slidebrook software (Intelligent Imaging Inovations, Denver, Colo.) using a 40× air ELWD objective (Zeiss) with 1 μm step size. The height (start and end point) of Z stacks were manually adjusted for all 701 RNAi conditions.

By visual inspection of ~96,000 images, the percentage of multipolar spindles for each RNAi condition was scored. The screening results are summarized below in Table 1.

TABLE 1

Summary of RNAi Screen Results in S2 Cells

|  | Number |
|---|---|
| Total Screened | 23,172 dsRNAs |
| Not determined (# spindle <10) | 148 |
| Scored as hits in primary screen | 701 genes |
| Tested hits from primary screen | 292 genes |
| Total hits after secondary screen | 133 (46%) genes |
| Hits with mammalian homologs | 82 (62%) genes |

Using a 95% confidence interval, the primary screen identified 701 candidates associated with a multipolar spindle phenotype. 292 genes were selected as initial cohort for further study based on: the strength of the phenotype, the existence of readily identifiable mammalian homologues, and few or no predicted off-target effects. Additionally, most genes that were previously determined to be required for cytokinesis in *Drosophila* cells were eliminated (Echard, A. et al. (2004) *Curr Biol* 14:1685-1693; Eggert, U.S. et al. (2004) PLoS Biol 2:e379) because spindle multipolarity can be a secondary effect of cytokinesis failure (Goshima, G. et al. (2007) *Science* 316:417-421). Of the 292 genes selected for the secondary screen, 133 were confirmed to have a bona fide role in centrosome clustering. Among the validated genes, 62% of the genes identified (83 out of 133 genes) have mammalian homologues, while 33% of the genes (44) do not have a known function. Centrosome clustering can occur with varying efficiency. The following classes of defects were distinguished: bipolar spindles with multiple centrosomes scattered around the spindle, small multiaster spindles and large multipolar spindles.

The screen identified genes involved in a diverse range of cellular processes, suggesting unappreciated complexity in the mechanisms controlling organization of supernumerary centrosomes, including a number of genes that promote the bundling of spindle MTs, for example, the minus end-directed kinesin Ncd (human HSET), The screen also identified genes in unexpected processes. The discovery of genes required for the SAC, actin, cell polarity and cell adhesion suggested novel mechanisms that suppress multipolar mitoses. Below are presented experiments that define three overlapping mechanisms that suppress multipolar mitoses: a timing mechanism employing the SAC, intrinsic pole clustering mechanisms relying on MT regulators, and a novel mechanism requiring actin and cell adhesion.

Example 2

The Spindle Assembly Checkpoint (SAC) Prevents Multipolar Mitoses

Figure 2:
FIG. 2 is a bar graph of the percentage of S2 cells with abnormal spindles upon RNAi knockdown of EGFP or Mad2 alone, or RNAi knockdown of EGFP or Mad2 plus treatment with MG132.

The SAC components Mad2. BubR1 (human Bub1) and CENP-Meta (human CENP-E) are required for centrosome clustering. FIG. 2 illustrates that Mad2 is required for centrosome clustering. Centrosome clustering defects were scored in S2 cells upon RNAi of EGFP, Mad2 alone and EGFP or Mad2 plus 7 hours of MG132 treatment. The graph of FIG. 2 shows the average of three independent experiments (mean±Sd, *p<0.05; ***p<0.001, Student's t test).

The results shown in FIG. 2 indicate a role for the SAC in the process of centrosome clustering. This requirement was even more evident in cells that were not treated with MG132, indicating that the short treatment with MG132 employed in the screen partially masked the effect of SAC gene RNAi on spindle multipolarity. This finding was somewhat surprising, given previous work in PtK1 cells suggesting that the SAC is not activated by multipolar spindles or multiple centrosomes (Sluder, G. et al. (1997) *J Cell Sci* 110 (Pt 4): 421-429).

Time-lapse imaging supported a role for the SAC in preventing multipolar mitoses. In S2 cells where centrioles and MTs were labeled with GFP-SAS-6 and mCherry α-tubulin, there was a clear correlation between an increased number of centrosomes and a prolonged time required to form a bipolar spindle (2.7 fold). The interval between NEBD and anaphase onset was measured (visualized with GFP-Cid, *Drosophila* CENP-A) comparing cells with 2 or >2 centrosomes. Relative to cells with 2 centrosomes, cells with multiple centrosomes exhibited a marked delay in anaphase onset (1.8 fold). Moreover, the delay in anaphase onset was abolished by Mad2 RNAi, and these cells entered anaphase with declustered centrosomes and misaligned kinetochores. Further suggesting SAC activation, multipolar preanaphase spindles had a strong increase in the number of BubR1 foci relative to bipolar metaphase spindles. Finally, the requirement for the SAC to prevent multipolar mitoses can be partially suppressed by an artificial metaphase delay imposed by treatment with MG132. This suggests that the SAC does not monitor multipolar mitosis per se but rather that SAC activation, likely triggered by abnormal kinetochore attachment or tension, provides sufficient time for compensatory mechanisms to organize multiple centrosomes.

Example 3

Spindle-Intrinsic Pole Clustering Forces Prevent Multipolar Mitoses

Previous work in S2 cells has demonstrated a critical role for MT motors and MAPs in spindle pole focusing (Goshima, G. et al. (2005) *J Cell Biol* 171:229-240; Morales-Mulia, S. and Scholey, J. M. (2005) *Mol Biol Cell* 16:3176-3186). The screen described in Example 2 1 identified Ncd, a Kinesin-14 family member, as the strongest hit in the primary screen. Ncd is a minus end-directed motor that bundles MTs at the spindle poles (Karabay, A. and Walker, R. A. (1999) *Biochemistry* 38:1838-1849). By GFP-SAS-6 labeling, it was demonstrated that Ncd is required to cluster multiple centrosomes. *Drosophila* dynein was not identified in the screen. This is expected because in S2 cells loss of dynein does not significantly induce multipolar mitoses, although it does compromise centrosome attachment and tight focusing of the spindle poles (Goshima, G. et al. (2005) *J Cell Biol* 171:229-240). Further validation of the screen confirmed the role of the MAP Asp in pole focusing (Morales-Mulia, S. and Scholey, J. M. (2005) *Mol Biol Cell* 16:3176-3186; Wakefield, J. G. et al. (2001) *J Cell Biol* 153:637-648).

Additionally, the screen identified several other factors that contribute to the intrinsic cohesion of spindle MTs. A requirement for Bj1/RCC1 (RanGEF) in centrosome clustering was identified, consistent with its role in preventing multipolar mitosis in mammalian cells (Chen, T. et al. (2007) *Nat Cell Blot* 9:596-603). Roles for the ADP-ribosylation factors Tankyrase and CG15925, a putative human PARP-16 homolog were also identified (Schreiber, V. et al. (2006) *Nat Rev Mol Cell Biol* 7:517-528). ADP-ribosylation by tankyrase is thought to contribute to spindle bipolarity by providing a static matrix that may anchor MT motors and other spindle proteins (Chang, P. et al. (2005) *Nat Cell Biol* 7:1133-1139.). A role for PARP-16 in mitosis has not been previously described.

Example 4

Actin-Dependent Forces Regulate Spindle Multipolarity

In addition to genes that likely contribute to the bundling and organization of spindle MTs, unexpectedly, genes involved in the organization and regulation of the actin cytoskeleton, such as the formin Form3/INF2 were also identified (Chhabra, E. S. and Higgs, H. N. (2006) *J Biol Chem* 281:26754-26767). Knockdown of these genes does not induce multipolar mitoses indirectly by triggering cytokinesis failure. Experiments using a brief (2 hr) treatment with small molecules that disrupt the actin cytoskeleton similarly induce multipolar mitoses.

Figure 3:
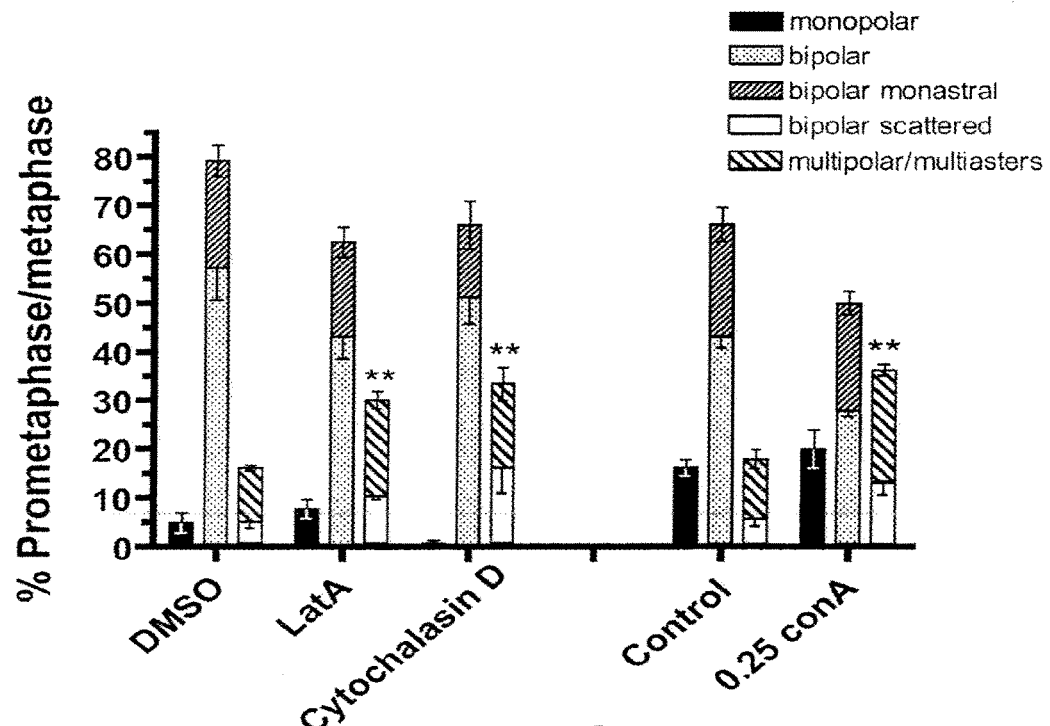
FIG. 3 is a bar graph of the percentage of S2 cells with abnormal spindles upon treatment with Latrunculin (LatA), Cytochalasin D or Concanavalin-A (Con-A).

More specifically, cells were treated with Latrunculin (40 µM LatA), Cytochalasin D (20 µM) for 2 hours and the percentage of centrosome clustering defects was determined. The results are shown in FIG. 3, which demonstrates the requirement for the actin cytoskeleton for centrosome clustering in S2 cells. The graph shows the average of three independent experiments (mean±SD, *$p<0.05$; **$p<0.005$, Student's t test).

Furthermore, live cell imaging of S2 cells revealed that actin is indeed required for the initial clustering of multiple centrosomes. Relative to controls (14.7±6.4 min), there was a 1.5 fold delay in centrosome clustering in 13/15 LatA-treated cells (22.1±12.3 min). The remaining 2/15 cells completely failed to cluster extra centrosomes. The cell cycle delay induced by LatA treatment is likely due to activation of the SAC, as evidenced by prominent labeling of kinetochores with BubR1 in LatA-treated cells.

Next, it was determined if cortical contraction is required for centrosome clustering. Cells were exposed, for 2 hours, to soluble tetravalent lectin concanavalin A (Con-A), which crosslinks the plasma membrane and thus globally blocks cortical contraction (Canman, J. C. and Bement, W. M. (1997) *J Cell Sci* 110 (Pt 16):1907-1917). The percentage of centrosome clustering defects after Con-A treatment was determined. The results also are shown in FIG. 3, which demonstrates that Con-A treatment induced centrosome clustering defects.

Furthermore, it was found that enhancing myosin-based contractility can suppress spindle multipolarity. Low concentrations of calyculin A (CA) inhibit the myosin light chain phosphatase (MLCP) and promote myosin II activation without altering its distribution (Gupton, S. M. and Waterman-Storer, C. M. (2006) *Cell* 125:1361-1374). Wild type S2 cells treated with CA had a modest decrease in centrosome clustering defects (15% to 9%). Moreover, CA treatment partially rescued the centrosome clustering defect induced by Ncd RNAi. Thus, in cells with extra centrosomes, actin and actin-based contractility influence whether mitosis is bipolar or multipolar.

It was also determined whether the actin and intrinsic spindle forces act cooperatively to prevent multipolar mitoses. Indeed, LatA treatment in Ncd or Bj1/RCC1-depleted cells resulted in a combinatorial increase in spindle multipolarity. To farther evaluate this idea, time-lapse spinning disc microscopy was used to define the trajectory of centrosome movement in Ncd-depleted S2 cells. In contrast to control cells, centrosomes in Ncd-depleted cells exhibited a striking increase in mobility; both the speed and extent of movement was increased. Moreover, the bulk of the centrosome movement was directed away from the spindle and towards the cell cortex. The mobility of centrosomes in Ncd-depleted cells was severely diminished by transient exposure of cells to LatA, demonstrating an actin requirement for these cortical pulling forces. Thus, cortical forces collaborate with intrinsic spindle bundling forces to organize multiple centrosomes.

These results also provided insight into the nature of the cortical force generators that regulate spindle multipolarity. It was found that the MT+tip CLIP-190 and the myosin Myo10A are important for centrosome clustering. *Drosophila* Myo10A is a human Myo15 homolog that can bind MTs via a unique MyTH4-FERN domain. Myo10, a member of mammalian MyTH4-FERM-containing myosin, is known to be required for spindle positioning (Sousa, A. D. and Cheney, R. E. (2005) *Trends Cell Biol* 15:533-539; Toyoshima, F. and Nishida, E. (2007) *EMBO J* 26:1487-1498; Weber, K. L. et al. (2004) *Nature* 431:325-329). RNAi of Myo10A but not the other *Drosophila* MyTH4-FERM-containing myosin Myo7 induced a 2-fold increase in centrosome clustering defects without cytokinesis failure (Eggert, U.S. et al. (2004) *PLoS Biol* 2, e379). Moreover, knockdown of Myo10A did not have an additive effect on spindle multipolarity if cells were concomitantly treated with LatA. Finally, centrosome tracking of Myo10A-depleted cells revealed a similar effect on centrosome movement as LatA treatment; in cells depleted of Myo10, only random or greatly reduced movements of centrosomes were detected in contrast to the extensive cortically-directed movement shown in Ncd depleted cells. Together, the data demonstrate that multiple centrosomes are organized combinatorially by spindle-intrinsic forces and by actin-dependent cortical forces acting at least in part on astral MTs.

Example 5

Cell Shape, Cell Polarity and Adhesion Effects on Spindle Multipolarity

The screen identified a requirement for genes implicated in cell adhesion for centrosome clustering: Turtle, Echinoid, Cad96Ca, CG33171, and Fit1. The *Drosophila* FERM domain containing protein Fit1 appears to have a highly conserved function in regulating cell-matrix adhesion in higher eukaryotes (Rogalski, T. M. et al. (2000) *J Cell Biol* 150:253-264; Tu, Y. et al. (2003) *Cell* 113:37-47). The mammalian Fit1 homolog, Mig-2/human PLEKHC1, localizes to focal adhesions (FAs) and is important for integrin-mediated cell adhesion and modulation of cell shape by linking integrins to actin cytoskeleton (To, Y. et al. (2003) *Cell* 113:37-47). The uncharacterized CG33171 protein has homology to mammalian Col18A, previously implicated in the regulation of cell matrix adhesion (Dixelius, J. et al. (2002) *Cancer Res* 62:1944-1947; Wickstrom, S. A. et al., (2004) *J Biol Chem* 279:20178-20185). Turtle and Echinoid containing fibronectin type-III domains are involved in cell-cell adhesion (Bodily, K. D. et al. (2001) *J Neurosci* 21:3113-3125; Wei, S. Y. et al. (2005) *Dev Cell* 8:493-504). In addition, the posterior/lateral polarity gene PAR-1 (PAR-1/MARK/KIN1 family member) and the apical polarity genes Crumbs and Cornetto were identified, which are important for astral MT function, asymmetric cell division and epithelial polarity (Bulgheresi, S. et al. (2001) *J Cell Sci* 114:3655-3662; Munro, E. M. (2006) *Curr Opin Cell Biol* 18:86-94; Tepass, U. et al. (2001) *Annu Rev Genet* 35:747-784). A number of these genes have previously been identified because of their requirement to maintain normal interphase cell shape and adhesion. Indeed, LatA treatment or Myo10 depletion showed no enhancement of spindle multipolarity when combined with depletion of CG33171, Fit1, Crumbs, Cornetto, or PAR-1 proteins, demonstrating that these genes influence centrosome clustering via the actin cytoskeleton.

Example 6

Conservation of the Mechanisms to Prevent Multipolar Mitoses

It was next determined if mammalian cancer cells utilize similar mechanisms to cluster multiple centrosomes as observed in S2 cells. This was done to establish the relevance of the screen to human cancer and because of techniques utilizing mammalian cancer cells that enabled direct characterization of adhesion and cell shape effects on multipolar mitoses. Although there is some variability in its efficiency, clustering of extra centrosomes is commonly observed in mammalian cells.

Figure 4:
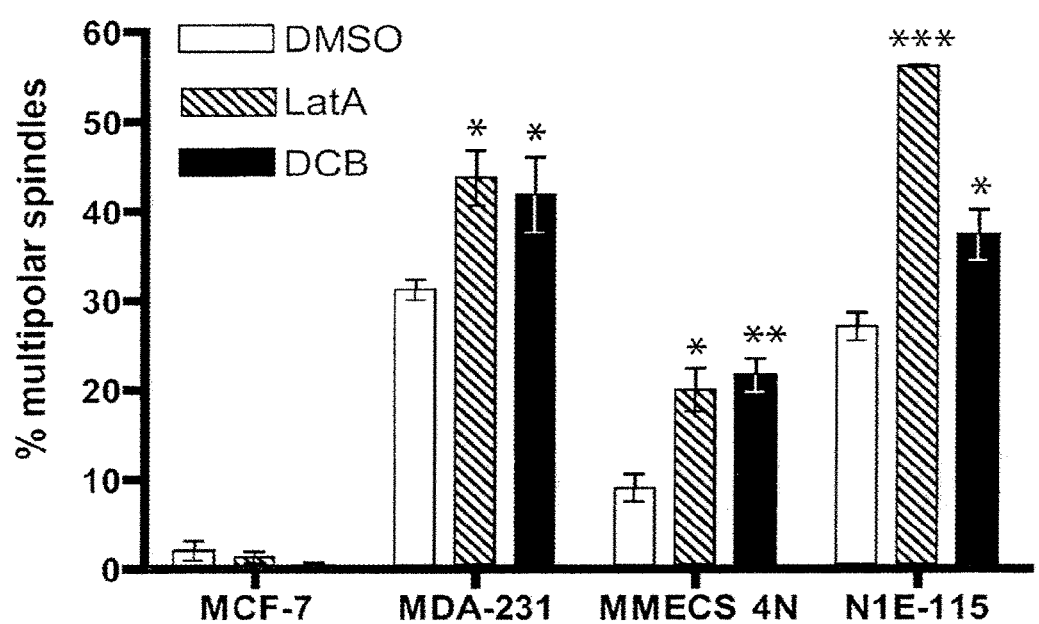
FIG. 4 is a bar graph of the percentage of cells with multipolar spindles in MCF-7, MDA-231, MMECS 4N or N1E-115 cells upon treatment with DMSO, LatA or DCB

To determine the effect of transient actin disruption in mammalian cells, the cell lines MCF-7, MDA-231, MMEDX 4N and N1E-115 were treated with DMSO, LatA (5 μM) or Dihydrocytochalasin B (DCB) (10 μM) for 2 hours. The MCF-7 cell line contains 2 centrosomes whereas the other cell lines contain greater than 2 centrosomes. The results are shown in FIG. 4. The graph shows the average of three independent experiments (mean±SD; *p<0.05; p<0.005; *p<0.001, Student's t test). As illustrated in FIG. 4, transient actin disruption led to a significant increase in the frequency of multipolar spindles in cell lines that contained multiple centrosomes but not in cells with normal centrosome number. These multipolar spindles result from declustering of extra centrosomes and were not due to the splitting/fragmentation of centrioles. Actin presumably influences centrosome positioning via forces on astral MTs. Consistent with this idea, low dose nocodazole treatment, selectively disassembling astral MTs (Thery, M. et al. (2005) *Nat Cell Biol* 7:947-953), increased the frequency of multipolar spindles specifically in cells with extra centrosomes.

The parallel between *Drosophila* and mammalian cells extended to the genetic requirements for centrosome clustering. To examine this further, siRNA experiments were performed with mammalian HSET (Ned homolog) and Myo10 genes, as follows. Mixed pools (ON-TARGETplus and SMART pools) of 4 different oligos of siRNAs against human HSET, human Myo10 and mouse Myo10 were purchased from Dharmacon, siRNA against mouse HSET was purchased from Ambion. Non-specific scrambled siRNA was used as control (Ambion). The oligo sequence of the siRNAs are set forth below in Table 2:

TABLE 2 siRNA Oligo Sequences

| | Oligo Sequence 5'-3' | siRNA ID# | SEQ# |
|---|---|---|---|
| Human HSET | UAACUGACCCUUUAAGUCCUU | J-004958-06 | 1 |
| | AGUGUUGUGCGCUCUGUCCUU | J-004958-07 | 2 |
| | GACACAAGCACGCAAGUUCUU | J-004958-08 | 3 |
| | UGGUCCAACGUUUGAGUCCUU | J-004958-09 | 4 |
| Human Myo10 | CAAGUUGAGAUUUAUGUCCUU | J-007217-05 | 5 |
| | UAAGACAUCAGCUACGACGUU | J-007217-06 | 6 |
| | UAAUCUACAAUUCUCCCGCUU | J-007217-07 | 7 |
| | AUUCCCUGAAAUUUCCUCCUU | J-007217-08 | 8 |
| Mouse HSET | GGCUAAUAAGAAGUGAAGtt | 287750 | 9 |
| | GGAACUGAAGGGCAAUAUCtt | 287751 | 10 |
| | GGCCAUUAACAGCAGUCUGtt | 287752 | 11 |
| Mouse Myo10 | UUCCACGGUGCCCUUGAGCUU | J-062004-09 | 12 |
| | UUCUCCUCGCUAUCGUUUUUU | J-062004-10 | 13 |
| | UUUCUUGUGCAGCCAGCCUUU | J-062004-11 | 14 |
| | UACAUCAGCUUCGACUGGCUU | J-062004-12 | 15 |

Figure 5:
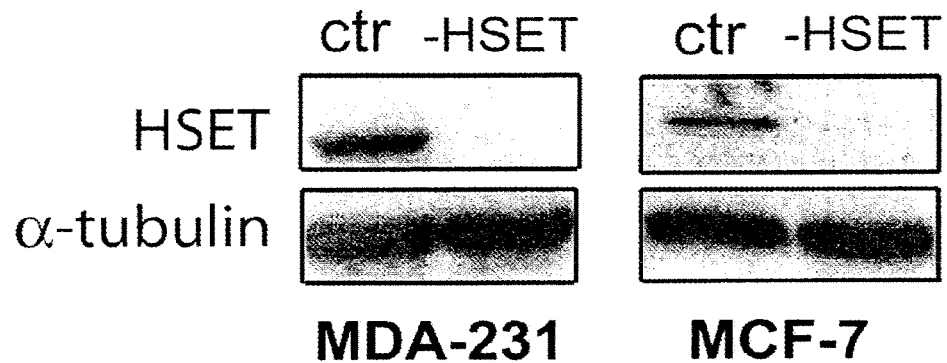
FIG. 5 is a Western blot showing the depletion of HSET after three days of siRNA in MDA-231 and MCF-7 cells.
Figure 6:
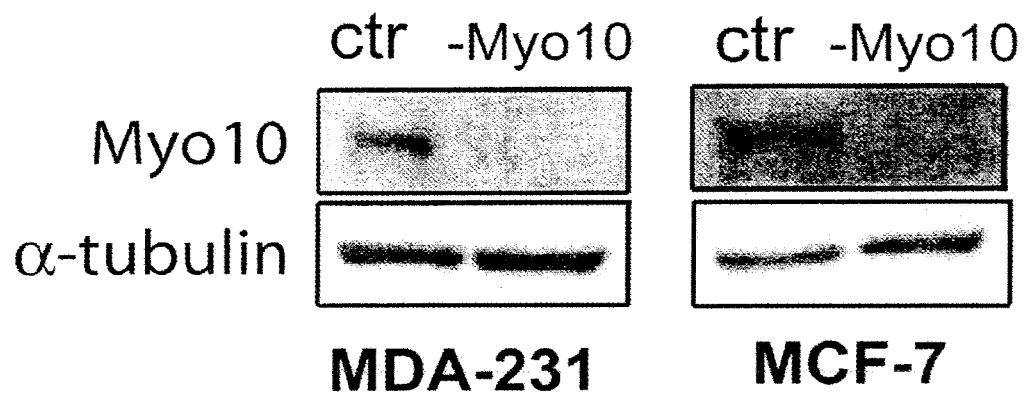
FIG. 6 is a Western blot showing the depletion of Myo10 after three days of siRNA in MDA-231 and MCF-7 cells.
Figure 7:
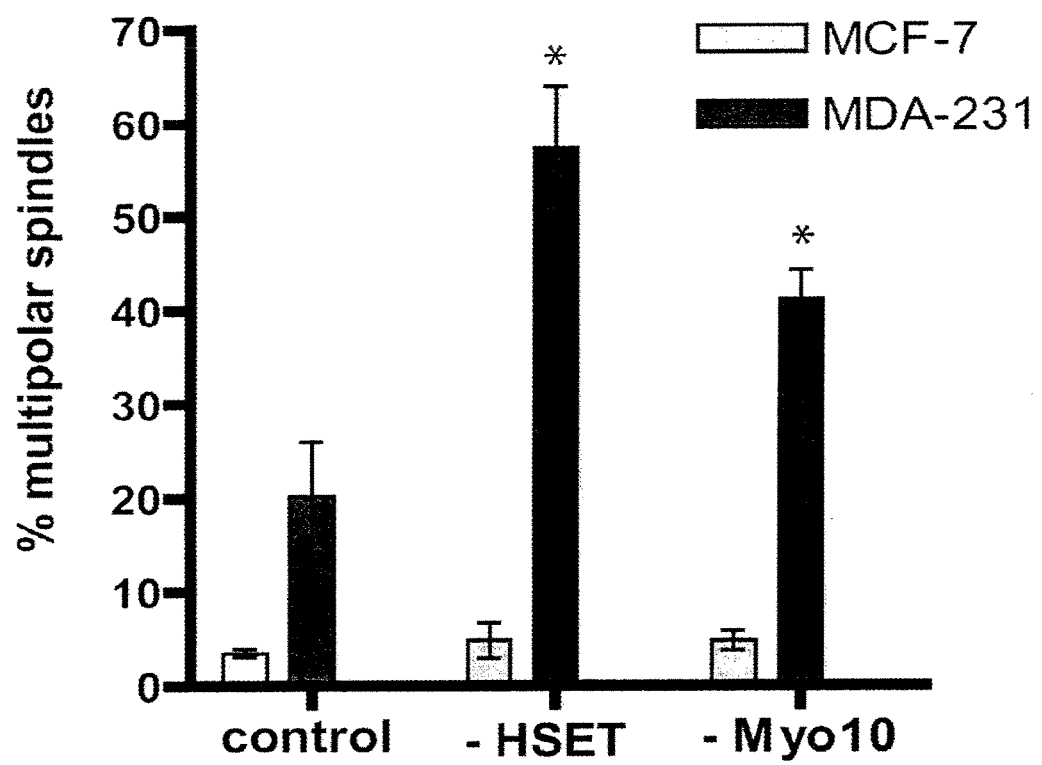
FIG. 7 is a bar graph showing the percentage of cells with multipolar spindles in MCF-7 or MDA-231 cells upon treatment with siRNA of HSET or Myo10.

Cells were transfected with Lipofectamine RNAiMAX (Invitrogen) with a final siRNA concentration of 50 nM according to the manufacturer's instructions. Cells were analyzed/harvested three days after transfection (unless specified otherwise). FIGS. 5 and 6 show the results of Western blots showing the depletion of HSET (FIG. 5) or Myo10 (FIG. 6) after three days of siRNA in MDA-231 and MCF-7 cells. FIG. 7 is a bar graph showing the percentage of cells with multipolar spindles in MCF-7 or MDA-231 cells upon treatment with siRNA of HSET or Myo10. The results shown in FIG. 7 demonstrate that siRNA of the Ncd homolog HSET (a Kinesin-14 member) and Myo10 increased the frequency of multipolarity, specifically in cells harboring multiple centrosomes (i.e., MDA-231 cells). As in S2 cells, Myo10-induced multipolarity is not a consequence of cytokinesis failure.

Figure 8:
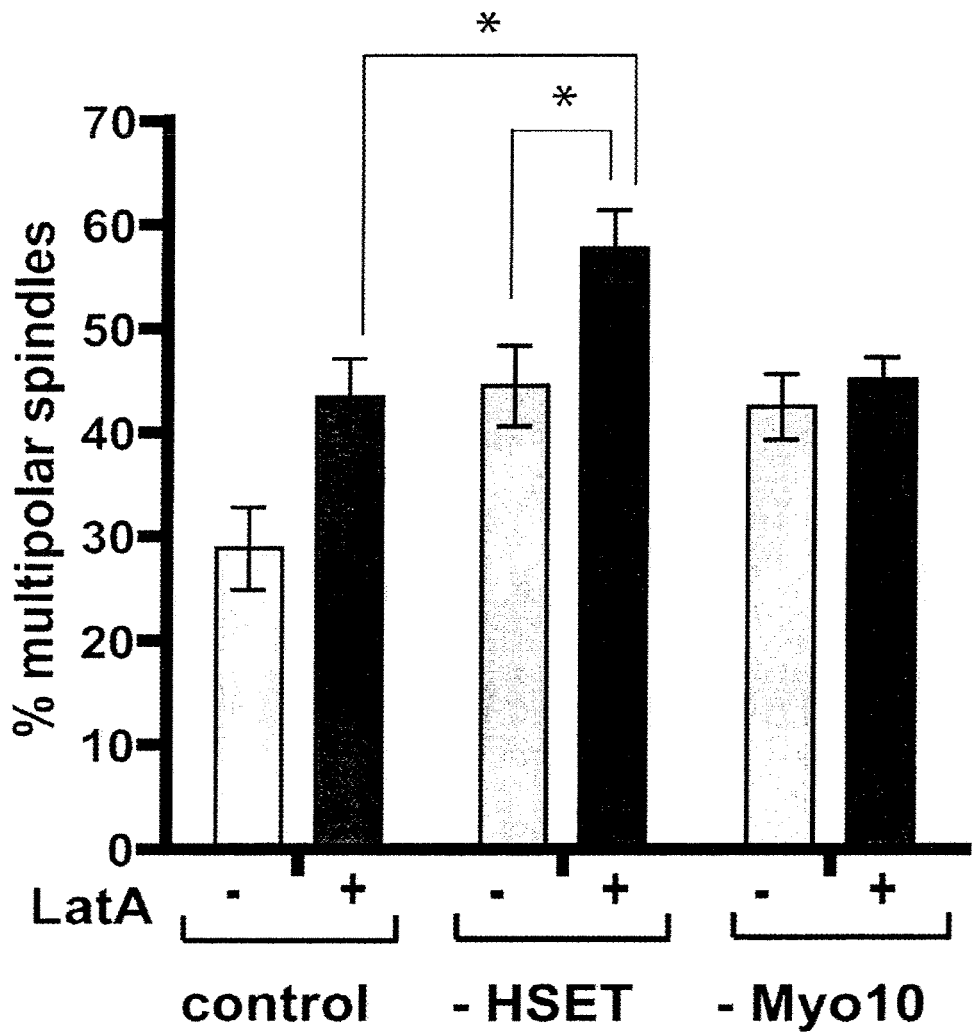
FIG. 8 is a bar graph showing the percentage of mitotic cells with multipolar spindles upon treatment with siRNA of HSET or Myo10, both with (+) or without (−) LatA.

Finally, it was determined whether the cortical actin cytoskeleton influences centrosome organization in parallel with intrinsic spindle pole clustering forces, by treatment with siRNA of HSET or Myo10 in combination with the actin disruption agent LatA. As shown in FIG. 8, disruption of both actin and HSET had a combinatorial effect, increasing the frequency of multipolar spindles relative to the individual treatments. When Myo10 siRNA is combined with LatA treatment no such effect was observed. Thus, similar overlapping mechanisms prevent multipolar mitoses in mammalian cancer cells and *Drosophila* S2 cells.

Example 7

Interphase Cell Shape, Adhesion and Multipolar Mitoses

Although cells round up in mitosis, they preserve a memory of their interphase shape by retaining actin-containing retraction fibers (RFs) linked to sites of strong cell-matrix adhesion (Mitchison, T. J. (1992) *Cell Motil Cytoskeleton* 22:135-151; Thery, M. and Bornens, M. (2006) *Curr Opin Cell Biol* 18:648-657). The interphase adhesion pattern and the distribution of actin-containing RFs are known to strongly influence spindle orientation during mitosis (Thery, M. et al. (2007) *Nature* 447:493-496; Thery, M. et al. (2005) *Nat Cell Biol* 7:947-953). The finding from the screen that preventing multipolar mitoses requires both cell matrix adhesion genes and actin regulators, suggested an appealing hypothesis: these gene products could act cooperatively to organize extra centrosomes by affecting the distribution and/or the composition of retraction fibers (RFs) and thus cortical force generators.

Several lines of evidence support this hypothesis. First, live-cell imaging was used to correlate interphase cell shape with the pattern of cell division during mitosis. MDA-231 (breast cancer cells containing extra centrosomes) that assumed an elongated or polarized shape in interphase, almost uniformly underwent bipolar divisions. By contrast, MDA-231 cells that assumed a round shape in interphase had an increased frequency of multipolar divisions. Second, in tetraploid BSC-1 cells, whose thick RFs are readily visualized by DIC imaging, it was noted that a strong correlation between the positioning of the RFs and whether cells underwent a bipolar (bipolar distribution of RFs) or multipolar division (isotropic distribution of RFs). Third, RFs accumulate specific proteins, such as the ERM protein ezrin, which are implicated in cortical heterogeneity and thus local force generation on astral MTs. Disruption of this cortical heterogeneity by the src kinase inhibitor PP2 (Thery, M. et al. (2005) *Nat Cell Biol* 7:947-953), also induced multipolar spindles in MDA-231 but not in MCF-7 cells. Fourth, to evaluate the role of cell matrix adhesion for the efficiency of mitosis, cells were plated on different concentrations of fibronectin (FN) to vary the strength of cell-matrix attachment. Concentrations of FN that inhibit focal adhesion (FA) turnover (30 μg/ml) increased the frequency of multipolar spindles in MDA-231 cells but not in MCF-7 cells. Moreover, this effect could be reversed by CA, which promotes FA turnover by increasing cortical contractility (Gupton, S. L. and Waterman-Storer, C. M. (2006) *Cell* 125:1361-1374).

To directly test the role of the cell adhesion pattern and RF positioning in centrosome clustering, micro-contact printing of FN was used to manipulate cell adhesion patterns (Thery, M. et al. (2005) *Nat Cell Biol* 7:947-953). MDA-231 cells plated onto Y-shaped or O-shaped micropatterns had a significant (3-4 fold) increase of multipolar spindles compared to the controls. In contrast, plating cells on H-shaped micropattern suppressed the frequency of multipolar spindles relative to control cells (2%, half of the control). Thus, O and Y arrangements of adhesive contacts bias cells into multipolar mitoses whereas bipolar arrangements of adhesive contacts (H-shape) promote bipolar mitoses. These findings demonstrate that interphase cell adhesion pattern, and thus cell shape, can have a remarkable influence on the fidelity of mitosis—specifically in cancer cell containing extra centrosomes.

Example 8

Disruption of Centrosome Clustering can Selectively Kill Cancer Cells

In principle, disruption of centrosome clustering could have a selective effect on the viability of cancer cells containing multiple centrosomes because most somatic cells have two centrosomes during mitosis. As a first step towards evaluating this potential therapeutic strategy, the sensitivity of different cancer cell lines to knockdown of HSET was determined.

HSET is a particularly interesting therapeutic target because it is non-essential for cell division in normal cells and kinesins are amenable to small molecule inhibition (Mayer, T. U. et al. (1999) *Science* 286:971-974; Mountain, V. et al. (1999) *J Cell Biol* 147:351-366). Depletion of HSET by siRNA leads to an increase in multipolar spindles in human cancer cells containing multiple centrosomes (see FIG. 7, described further in Example 6 above). To determine the consequences of centrosome de-clustering, cell division was monitored in multiple cell lines that contain extra centrosomes using DIC microscopy. Depletion of human HSET, confirmed with 3 independent siRNAs, induced a dramatic increase in multipolar anaphases (88%) in N1E-115 cells in which nearly 100% of cells contain extra centrosomes (Spiegelman, B. M. et al. (1979) *Cell* 16:253-263). A similar result was obtained with MDA-231 cells where ~50% of cells contain extra centrosomes (24% after HSET depletion) and with tetraploid BJ and NIH-3T3 cells with extra centrosomes. By contrast, HSET knockdown had no effect on cell division in a variety of diploid control cells.

Figure 9:
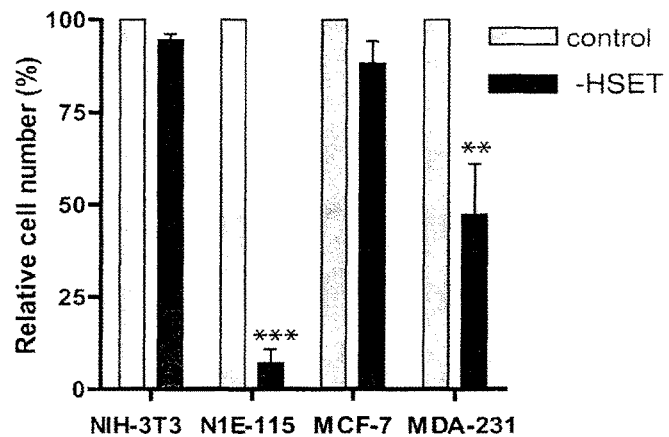
FIG. 9 is bar graphs showing the loss of cell viability and inhibition of colony formation by N1E-115 cells after 6 days HSET siRNA treatment.

FIG. 9 illustrates the loss of cell viability and inhibition of colony formation by N1E-115 cells after 6 days of HSET siRNA. FIG. 9 shows relative cell number in control and HSET-depleted (−HSET) cells from three independent experiments after six days post transfection (left panel) and the average colony number from two independent experiments in 4 different areas (right panel; area=10 mm$^2$). Strikingly, depletion of HSET from N1E-115 cells for 6 days, by siRNA treatment, reduced cell viability more than 90%, and many of the surviving cells were shown to be senescent.

Figure 10:
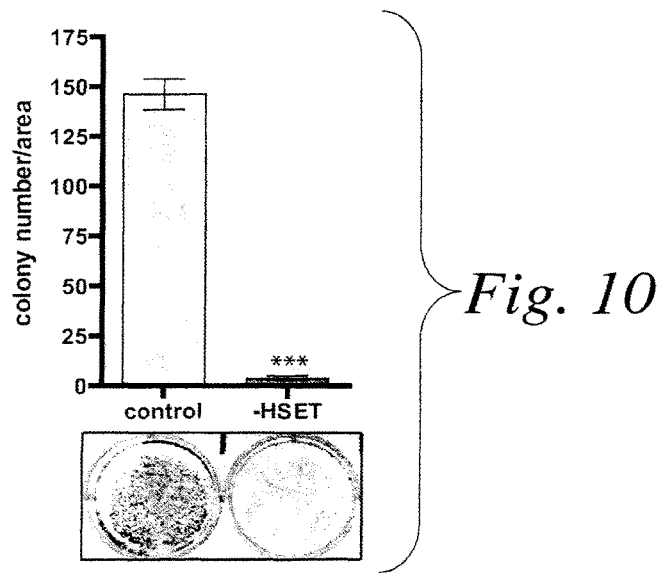
FIG. 10 is a bar graph showing HSET RNAi-induced cell death in various cancer cell lines in proportion to the fraction of cells with extra centrosomes.

FIG. 10 illustrates HSET RNAi-induced cell death in various cancer cell tines in proportion to the fraction of cells with extra centrosomes. The bar graph shows relative cell number in control and HSET-depleted (−HSET) cells after six days post-transfection with siRNA. The percentage of cells with greater than 2 centrosomes is indicated below in the graph. The graph shows the average of three independent experiments. All graphics represent mean±SD ($p<0.005$, *$p<0.001$, Student's t test). Thus, HSET depletion induced cell death in various cancer cells lines in rough proportion to the fraction of cells containing extra centrosomes. In contrast, the viability of cells that mostly possess two centrosomes was only slightly reduced in the absence of HSET. Thus, centrosome de-clustering can induce cell death selectively in cells with supernumerary centrosomes.

What is claimed is:

1. A method for identifying a compound that inhibits activity of meiotic kinesin HSET, the method comprising:
    (a) providing an indicator composition comprising:
        a sample from a tumor, wherein at least 50% of tumor cells comprise supernumerary centrosomes, and the meiotic kinesin HSET;
    (b) contacting the indicator composition with a test compound; and
    (c) determining activity of the meiotic kinesin HSET in the presence of the test compound,
        wherein reduction of activity of the meiotic kinesin HSET in the presence of the test compound, as compared to activity of the meiotic kinesin HSET in the absence of the test compound identifies the test compound as the compound that inhibits the activity of a meiotic kinesin HSET,
        wherein the compound that inhibits activity of meiotic kinesis HSET, when administered to the sample, inhibits the meiotic kinesis HSET causing:
            disruption of the clustering of extra centrosomes in the at least 50% of the tumor cells comprising supernumerary centrosomes, and
            promotion of multipolar mitoses to selectively induce cell death of the at least 50% of the tumor cells comprising supernumerary centrosomes;
        wherein the determining activity comprises measuring at least one of HSET mRNA, HSET protein expression levels, one or more enzymatic activities or biological activities of HSET, HSET ATPase activity, microtubule binding activity and centrosome clustering activity, or a combination thereof.

2. The method of claim 1, wherein the indicator composition is contacted with each member of a library of test compounds and one or more test compounds within the library are selected that inhibit the activity if the meiotic kinesin HSET.

3. The method of claim 1, wherein the compound that inhibits activity of meiotic kinesin HSET is selected from a kinesin-14 family member.

4. The method of claim 1, wherein the compound that inhibits activity of meiotic kinesin HSET is selected from the groups consisting of RNAi agent, an antisense agent, and a small molecule.

5. The method of claim 1, wherein the test compound that inhibits activity of meiotic kinesin HSET, upon administration of the compound to a subject with a tumor, wherein at least 50% of tumor cells comprise supernumerary centrosomes, is capable of causing
    (a) disruption of the clustering of extra centrosomes in the at least 50% of tumor cells comprising supernumerary centrosomes, and
    (b) promotion of multipolar mitoses to selectively induce cell death of the at least 50% of tumor cells comprising supernumerary centrosomes.

6. The method of claim 1, wherein the indicator composition is a cell that expresses HSET.

7. The method of claim 6, wherein the method of the cell that expresses HSET is a cell that naturally expresses HSET.

8. The method of claim 7, wherein the cell that expresses HSET is selected from the group consisting of MDA-231, MMEDX 4N and N1E-115.

9. The method of claim 6, wherein the cell that expresses HSET is a cell engineered to express or overexpress HSET.

10. The method of claim 1, wherein the indicator composition is a cell-free composition that comprises HSET.

* * * * *